US007285426B2

(12) United States Patent
Bohannon et al.

(10) Patent No.: US 7,285,426 B2
(45) Date of Patent: Oct. 23, 2007

(54) BULKING MATERIALS CONTAINING STARCH REAGENT FOR USE IN TEST DEVICES

(75) Inventors: Robert Bohannon, Chapel Hill, NC (US); Glen Chapman, Graham, NC (US); Alan Morris, Burlington, NC (US); Maria Scholz-Steele, Julian, NC (US); Martin Green, Greensboro, NC (US); Phillip Hartzog, Ramseur, NC (US); Oluyomi Adeneye, Greensboro, NC (US)

(73) Assignee: Medtox Scientific, Inc., Saint Paul, MN (US)

( * ) Notice: Subject to any disclaimer, the term of this patent is extended or adjusted under 35 U.S.C. 154(b) by 190 days.

(21) Appl. No.: 11/123,477

(22) Filed: May 5, 2005

(65) Prior Publication Data

US 2005/0255608 A1 Nov. 17, 2005

Related U.S. Application Data

(63) Continuation-in-part of application No. 10/946,963, filed on Sep. 21, 2004.

(60) Provisional application No. 60/568,805, filed on May 5, 2004, provisional application No. 60/564,768, filed on Apr. 22, 2004.

(51) Int. Cl.
*G01N 33/558* (2006.01)

(52) U.S. Cl. ............................ 436/514; 422/56; 422/57; 422/58; 435/6; 435/287.1; 435/287.2; 435/287.7; 435/287.9; 435/805; 435/810; 435/970; 436/8; 436/518; 436/530; 436/169; 436/176; 436/805; 436/810

(58) Field of Classification Search ............... None
See application file for complete search history.

(56) References Cited

U.S. PATENT DOCUMENTS

| | | | |
|---|---|---|---|
| 4,094,647 A | 6/1978 | Deutsch et al. |
| 4,168,146 A | 9/1979 | Grubb et al. |
| 4,313,734 A | 2/1982 | Leuvering |
| 4,361,537 A | 11/1982 | Deutsch et al. |
| 4,446,232 A | 5/1984 | Liotta et al. |
| 4,452,901 A | 6/1984 | Gordon et al. |
| 4,517,288 A | 5/1985 | Giegel et al. |
| 4,806,311 A | 2/1989 | Greenquist |
| 4,855,240 A | 8/1989 | Rosenstein et al. |
| 4,868,108 A | 9/1989 | Bahar et al. |
| 5,120,643 A | 6/1992 | Ching |
| 5,569,608 A | 10/1996 | Sommer |
| 5,591,645 A | 1/1997 | Rosenstein et al. |
| 5,656,503 A | 8/1997 | May et al. |
| 5,955,448 A | 9/1999 | Colaco et al. |
| 6,187,598 B1 | 2/2001 | May et al. |
| 6,534,320 B2 | 3/2003 | Ching et al. |
| 2007/0053900 A1 | 3/2007 | Liu et al. |

FOREIGN PATENT DOCUMENTS

WO  WO97/04801 A1  2/1997

OTHER PUBLICATIONS

Liao, Young-Hong et al.; "Protective Mechanism of Stabilizing Excipients against Dehydration in the Freeze-Drying of Proteins"; 2002, *Pharmaceutical Research*, vol. 19, No. 12, pp. 1654-1861.

*Primary Examiner*—Christopher L. Chin
(74) *Attorney, Agent, or Firm*—Townsend and Townsend and Crew, LLP

(57) ABSTRACT

The present invention provides methods, compositions, and kits for rapid detection of analytes in a sample. Surprisingly, it has been found that bulking materials having starch reagents effectively enhance chromatographic detection methods by providing component stability and controlled release. Thus, the novel components and methods disclosed herein provide a completely new modality of chromatographic analyte detection.

46 Claims, No Drawings

BULKING MATERIALS CONTAINING STARCH REAGENT FOR USE IN TEST DEVICES

CROSS-REFERENCES TO RELATED APPLICATIONS

This application claims the benefit of U.S. Provisional Application No. 60/568,805, filed May 5, 2004, and is a continuation-in-part of U.S. application Ser. No. 10/946,963 filed Sep. 21, 2004, which claims the benefit U.S. Provisional Application No. 60/564,768, filed Apr. 22, 2004, each of which are herein incorporated by reference in their entirety for all purposes.

BACKGROUND OF THE INVENTION

Numerous analytical methods have been developed for determining the presence or absence and/or quantifying the amount of various analytes in tissues and fluids of organisms, such as blood, urine, fecal material, or tissue biopsy. Lateral flow chromatography is, perhaps, one of the more common of these analytical methods.

Lateral flow chromatography assays and devices are well known to those of skill in the art (see, e.g., U.S. Pat. Nos. 5,569,608, 5,120,643, 5,656,503, 4,855,240, and 5,591,645, British Patent GB 2204398A, and European patent EP 0323605 B1) and such assays are commercially available on a retail or OEM basis for numerous analytes.

Lateral flow immunoassays typically involve the application of a liquid test sample suspected of containing an analyte to be detected to an application zone of a lateral flow (immunochromatographic) test strip. The strip is comprised of a matrix material (e.g., paper, nitrocellulose, etc., see, e.g., U.S. Pat. No. 5,569,608) through which the test fluid and analyte suspended or dissolved therein can flow by capillarity from the application zone to a detection zone where a visible signal, or absence of such, reveals the presence or absence of the analyte.

Typically, the strip will include means for immunospecifically binding the analyte to be detected with its specific binding partner (e.g., where the analyte is an antigen, the binding partner is an antibody or antibody fragment, and vice versa) which bears a detectable label. In one such scheme, as disclosed in U.S. Pat. No. 4,446,232, the strip contains an enzyme labeled, mobile binding partner for the analyte which is in a zone downstream from the sample application zone. If the analyte is present in the test sample, it will combine with its labeled binding partner to form a complex which will flow along the strip to a zone which contains a substrate for the enzyme label capable of providing a signal (e.g., a colored response) in the presence of the enzyme label.

The strip typically contains a zone in which an analyte is immobilized, so that the labeled binding partner which does not combine with analyte, due to absence of analyte in the sample, will be captured and thereby inhibited from reaching a zone downstream. There have been published various modifications of this technique, many of which involve some competitive specific binding system in which the presence or absence of analyte in the test sample is determined by the detection or lack thereof of labeled binding partner in a particular device zone. In U.S. Pat. No. 4,868,108 there is disclosed a similar scheme with the addition of an immobilized capture reagent for the enzyme labeled binding partner in a particular zone to concentrate the enzyme label and enhance its ability to react with the enzyme substrate and thereby render the assay more sensitive.

Not all of the schemes for immunochromatography rely on an enzyme labeled binding partner/enzyme substrate as providing the signal for detection of the analyte. In U.S. Pat. No. 4,806,311 there is disclosed a multizone test device for the specific binding assay determination of an analyte and an immobilized binding partner together with a downstream zone for receiving labeled reagent which migrates thereto from an upstream zone. The downstream zone contains an immobilized form of a binding substance for the labeled reagent. The labeled reagent bears a detectable chemical group having a detectable physical property such as a luminescent group (e.g. a fluorescent or phosphorescent moiety), radioisotopes and electroactive moieties. U.S. Pat. No. 4,313,734 describes the use of gold sols as labels for antibodies which are detectable.

Many lateral flow immunochromatography systems utilize particulate (microparticle) markers (e.g., gelatin, dyed latex, or colloidal gold) which are labeled with a binding partner (e.g., antibody or antigen) that binds the analyte of interest.

The microparticles or other detectable moieties attached to an analyte binding moiety (e.g., an antibody or antigen) are dried onto (or otherwise localized in) either a lateral flow chromatographic strip or onto a sample application pad (typically glass fiber) which in turn is affixed to one end of a strip of chromatographic medium such as nitrocellulose. Another material binding to the analyte of interest is affixed to the chromatographic medium at or near the end opposite to the end having the application pad.

The liquid sample to be analyzed is placed on the pad, causing the suspension of the microparticles into the liquid and allowing any analyte in the liquid sample to bind to the analyte-binding material attached to the microparticles. The liquid sample leaves the application pad by diffusion and capillary action and begins to migrate along the nitrocellulose strip carrying the microparticles down the strip along with the liquid. When the liquid containing the suspended microparticles arrives at the region of the chromatographic strip bearing the second binding material, the analyte (if present in the original sample) will form a bridge between the analyte-binding material on the microparticles and the analyte-binding material affixed to the strip, resulting in the immobilization of the microparticles at that point on the strip where the analyte-binding material is affixed. This immobilization of the microparticles results in a visible signal (e.g., a colored band or dot) at this point on the strip. If the analyte is not present in the sample, the microparticles will continue past this location on the chromatographic strip and a visible signal will not be produced.

It will be appreciated that other labels (e.g., fluorescent labels) besides microparticles can be utilized. In addition, a single chromatography strip can contain reagents to detect or quantify a number of different analytes.

It will also be appreciated that the lateral flow strip can use an analyte detection that does not involve an antibody-antigen recognition system. Thus, for example, the strip can be impregnated in a detection zone with a chemical that reacts with the analyte itself to produce a signal.

Existing lateral flow chromatographic devices often fail to provide sufficient stability to the components of the test device, such as peptides, proteins (e.g. antibodies and fragments thereof), ligands, and nucleic acids. In addition, currently existing devices do not provide adequate control over the time in which the analyte is allowed to bind to detectable reagents of the assay. By providing a novel bulking material, the present invention solves these and other needs.

BRIEF SUMMARY OF THE INVENTION

It has been discovered that, surprisingly, bulking materials having a starch reagent effectively enhance chromatographic detection methods by providing component stability and controlled release. Thus, the novel components and methods disclosed herein provide a completely new modality of chromatographic analyte detection.

In a first aspect, the present invention provides a test device for detecting the presence of an analyte in a sample. The device includes a chromatographic medium having a sample release zone. The sample release zone includes a bulking material having a starch reagent.

In an exemplary embodiment, the test device is a lateral flow test device used to detect the presence of an analyte in a sample. The device includes a chromatographic medium that, upon wetting, allows the sample to migrate through various zones that are in fluid communication. The chromatographic medium includes an analyte binding zone, an assay zone and a sample release zone. The analyte binding zone includes a mobile detectable analyte binding reagent capable of binding to the analyte to form a mobile reagent-analyte complex. The assay zone includes an immobilized assay reagent capable of immobilizing the mobile detectable analyte binding reagent. The sample release zone includes a bulking material having a starch reagent. The assay zone is in fluid communication with the analyte binding zone upon wetting of the chromatographic medium. The sample release zone is upstream of the assay zone and in fluid communication with the assay zone upon wetting of the chromatographic medium.

In another aspect, the present invention provides a method of stabilizing an antibody in a dry state. The method includes contacting the antibody with a bulking material. Bulking materials are described above and are equally applicable to the present methods. The bulking material includes a starch reagent.

In another aspect, the present invention provides methods of determining the presence or absence of an analyte in a sample using the test device of the present invention. The method includes contacting the analyte binding zone of the test device with a sample and allowing the sample to flow from the sample release zone to the assay zone.

In another aspect, the present invention provides kits for use in detecting the presence of an analyte in a sample. The kit includes a test device of the present invention.

DETAILED DESCRIPTION OF THE INVENTION

Introduction

The present invention provides methods, compositions, and kits for rapid detection of analytes in a sample. Surprisingly, it has been found that bulking materials having starch reagents effectively enhance chromatographic detection methods by providing component stability and controlled release. The methods and devices are useful in a variety of testing formats, including lateral flow fertility tests, drug of abuse tests, infectious disease tests, environmental tests, and food inspection tests.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore or another moiety.

"Peptide" refers to a polymer in which the monomers are amino acids and are joined together through amide bonds, alternatively referred to as a polypeptide or protein. Unnatural amino acids, for example, β-alanine, phenylglycine and homoarginine may also be included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid," refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Certain compounds of the present invention (such as the various reagents described below) can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. In addition, they may be present in any appropriate salt form.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

A "sample" as used herein, refers to a representative part or a single item from a larger group chosen for analysis using the methods and/or test device of the present invention. A variety of samples may be analyzed using methods and devices of the present invention. Samples include environmental or biological materials derived from a bodily, cellular, viral and/or prion source. Some samples are derived from biological fluids such as saliva, blood and urine. In some embodiments, the biological fluids include whole cells, cellular organelles or cellular molecules such as a protein, protein fragment, peptide, carbohydrate or nucleic acid. The biological material can be endogenous or non-endogenous to the source. For example, in one embodiment, the biological material is a recombinant protein harvested from a bacteria and engineered using molecular cloning techniques (see generally, Sambrook et al., *Molecular Cloning: A Laboratory Manual,* 2d ed. (1989) Cold Spring Harbor Laboratory Press, Cold Spring Harbor, N.Y., which is incorporated herein by reference). In another embodiment, the sample comprises a chemically synthesized biological material such as a synthetic protein, protein fragment, peptide, carbohydrate or nucleic acid.

The term "wetting," as used herein, means contacting with a liquid. The liquid may include, for example, organic solvents and/or aqueous solvents. For example, the chromatographic media may be wetted by contacting the chromatographic media with a liquid sample or with a liquid solvent, such as an organic solvent, water, or an aqueous solvent.

A "starch reagent," as used herein refers to a polymer of three or more glucose molecules. Starch reagents include "hydrolyzed starch reagents" which are hydrolyzed (including partially hydrolyzed) forms of starches found in plants, animals, and/or microbes, such as glycogen amylose, amylopectin, and cellulose.

A "sugar," as used herein refers to a naturally occurring simple sugar in linear or cyclic form. When in linear form, the simple sugar is an aldehyde or ketone derivative of a straight chain polyhydroxy alcohol. Typically, the sugar includes from three to six carbon atoms (e.g., aldotrioses, tetroses, pentoses, and hexoses). When in cyclic form, the sugar ring contains an oxygen heteroatom as in, for example, a pyranose or furanose sugar structure. A "sugar," as used herein, does not include non-natural sugar derivatives.

"A" or "an," as used in a claim of the present application, means at least one.

Test Devices

In a first aspect, the present invention provides a test device for detecting the presence of an analyte in a sample. The device includes a chromatographic medium having a sample release zone. The sample release zone includes a bulking material having a starch reagent. The chromatographic device may further include additional test zone(s) (e.g. reaction zones, detection zones, and the like), which are well known in the art of analyte testing.

The chromatographic medium used herein may include a porous, solid phase material that allows liquid samples to migrate into various reaction and detection zones. The migration may proceed through any appropriate means of chromatographic transport, such as capillary action, pressure, electrophoresis, gravity, and the like.

In an exemplary embodiment, the test device is a lateral flow chromatographic device. The use of a chromatographic medium for the detection of analytes is well known, especially in the art of lateral flow chromatographic assays (e.g. home pregnancy testing and rapid drug analysis testing). Lateral flow chromatographic test formats useful in the present invention are discussed in detail in the background section and, for example, in U.S. Pat. Nos. 5,120,643; 4,168,146, 4,517,288; 4,452,901; 4,094,647; 4,361,537; 6,187,598, and 6,534,320, which are herein incorporated by reference in their entirety for all purposes.

In an exemplary embodiment, the lateral flow chromatographic device is a "lateral flow chromatography strip." A lateral flow chromatography strip refers to a test strip utilized for lateral flow chromatography. Lateral flow (chromatography) assays typically involve the application of a liquid test sample suspected of containing an analyte to be detected. The sample may be applied to a lateral flow chromatographic strip. The strip includes a chromatographic media (e.g., paper, nitrocellulose, etc., see, e.g., U.S. Pat. No. 5,569,608) through which a liquid sample can flow by capillary action. Where the detection of the analyte utilizes an antibody or antibody fragment, the assay may be referred to as a lateral flow immunochromatography assay and the strip a lateral flow immunochromatography strip.

Although lateral flow chromatographic test devices are well known in the art, no currently known lateral flow chromatographic devices include starch reagent components for sample release and/or component stability. Therefore, the present invention is not limited by any particular chromatographic medium or test device format. Rather, the current invention encompasses all known lateral flow test device formats with the improvement of a sample release zone that includes a bulking material having at least one starch reagent. The devices of this invention can be readily assembled with any of a variety of commercially available lateral flow chromatography assays (e.g., Syntron Quick-Scan 6, Syntron Bioresearch, Carlsbad, Calif.; Avitar Visualine II, Avitar Technologies, Canton, Mass.; Determine HIV-½, Abbott Laboratories, Abbott Park, Ill.; Clear Blue and E.P.T., Inverness Medical, Waltham, Mass.; Tirage BNP Test, Biosite, Inc., San Diego, Calif.; QuickVue tests, Quidel Corporation, San Diego, Calif.; OSOM tests, Genzyme, Waltham, Mass.; Directigen, BD Diagnostic Systems, Sparks, Md.).

A variety of analytes may be detected using the methods of the present invention, including hormones, drugs of abuse, impurities, infectious agents, nucleic acids, and disease markers. Thus, the devices, methods and kits of the present invention are useful, for example, in fertility tests, (e.g., urine and serum pregnancy tests, and LH ovulation predicator tests; tumor marker tests); drug of abuse (DOA) tests (e.g., methamphetamine, amphetamine, morphine, cocaine, marijuana (THC), PCP, benzodiazepine, barbiturates, methadone, tricyclic, MDMA and multi-drug test formats); infectious disease tests (e.g. HIV, Hepatitis-B, Hepatitis-C, Syphilis, Chlamydia, HPV, Herpes); *H. Pylori* fecal test (e.g. legionella pneumonia urine test); biowarfare agents (anthrax, ricin toxin, smallpox); and food inspection (e.g. rotavirus test, aflatoxin, genetically modified organisms—GMOs).

Exemplary Lateral Flow Assay Formats

In an exemplary embodiment, the lateral flow test device used to detect the presence of an analyte in a sample includes a chromatographic medium that, upon wetting, allows the sample to migrate through various zones that are in fluid communication. The chromatographic medium typically includes an analyte binding zone, an assay zone and a sample release zone. The analyte binding zone includes a mobile detectable analyte binding reagent capable of binding to the analyte to form a mobile reagent-analyte complex. The assay zone includes an immobilized assay reagent capable of immobilizing the mobile detectable analyte binding reagent. The sample release zone includes a starch reagent (e.g. a partially hydrolyzed starch, such as maltodextrin), as described in more detail below.

The assay zone is in fluid communication with the analyte binding zone upon wetting of the chromatographic medium. The sample release zone is upstream of the assay zone and in fluid communication with the assay zone upon wetting of the chromatographic medium. Therefore, a liquid sample may migrate from the sample release zone to the assay zone.

In an exemplary embodiment, the sample is in liquid form and contains at least one analyte. The analyte is applied to the chromatographic medium thereby wetting the chromatographic medium. The mobile detectable analyte binding reagent binds to the analyte after the analyte enters the analyte binding zone, thereby forming a mobile reagent-analyte complex. The mobile reagent-analyte complex migrates to the assay zone. By detecting the presence or absence of the mobile detectable analyte binding reagent in the assay zone, the presence of an analyte in a sample may be determined.

The lateral flow test device may optionally include a control zone and/or a labeling zone. The control zone includes an immobilized capture reagent that binds to any labeled reporter agent, including a mobile detectable analyte binding reagent. The immobilized capture reagent binds to the mobile detectable analyte binding reagent and/or the mobile detectable analyte binding reagent portion of the mobile reagent-analyte complex. The control zone is downstream of the assay zone and in fluid communication with the assay zone upon wetting of the chromatographic medium.

The labeling zone includes a detectable labeling reagent capable of binding to the mobile detectable analyte binding reagent. The labeling zone is located downstream of the analyte binding zone and upstream of the assay zone. The labeling zone is in fluid communication with the sample release zone and the assay zone upon wetting of the chromatographic medium.

For reasons of clarity, the lateral flow test device may be discussed in terms of a single chromatographic medium having zones with individual components. However, it should be understood that test devices having more than one chromatographic medium are also within the scope of the invention. In addition, each chromatographic medium may include more than one type of zone, region and/or components thereof. For example, each chromatographic medium may include more than one analyte binding zone, assay zone, and/or sample release zone. Each zone may include more than one reagent within the zone. Thus, the methods of the present invention may be used to detect the presence of multiple analytes in parallel.

In some embodiments, the sample release zone partially or fully overlaps with the analyte binding zone. Thus, the sample release zone and the analyte binding zone may form a single zone, sometimes referred to herein as an release-binding zone. The release-binding zone includes one or more starch reagents and a mobile detectable analyte. The release-binding zone is in fluid communication with the assay zone upon wetting of the chromatographic medium.

The sample release zone may also form a zone that is separate and distinct from the analyte binding zone. Where the sample release zone is non-overlapping with the analyte binding zone, the sample release zone is in capillary contact with the analyte binding zone. The sample release zone may be upstream or downstream from the analyte binding zone. In an exemplary embodiment, the sample release zone is downstream from the analyte binding zone.

The sample release zone may be in capillary contact with the assay zone in addition to the analyte binding zone, upon wetting of the medium. The sample release zone is typically downstream of the analyte binding zone and upstream of the assay zone.

Analyte Binding Zone

The analyte binding zone includes a mobile detectable analyte binding reagent that is capable of binding to the analyte in a sample. A wide variety of mobile detectable analyte binding reagents are useful in the present invention.

Mobile detectable analyte binding reagents useful in conjunction with the present invention include those materials which are members of a specific binding pair, also referred to herein as a ligand and receptor binding pair. The ligand and receptor are related in that the receptor specifically binds to the ligand, being capable of distinguishing the ligand from other materials having similar characteristics. Exemplary binding pairs include any known specific ligand and receptor pair found in nature or constructed using recombinant techniques (e.g. fusion proteins), chemical synthesis, or immunonological methods including antibody or peptide expressing phage display libraries. Therefore, mobile detectable analyte binding reagents include any appropriate biomolecule, such as peptides, proteins, carbohydrates, steroids, nucleic acids, sugars (including simple and complex sugars), and natural or unnatural derivatives thereof.

For example, analytes in a sample may be recombinantly engineered to include a protein tag able to specifically bind a protein tag binder. The protein tag binder is, or forms a portion of, the mobile detectable analyte binding reagent. A wide variety of protein tag and tag binder pairs are known in the art and are useful in the present invention, including, for example: glutathione-S-transferase (GST) and Glutathione (GSH), maltose-binding protein and maltose, chitin-binding protein and cellulose, thioredoxin and Oligo-Glutamic acid, HA peptide and HA; His and NTA (Nitrilotriacetic acid, with a metal such as Ni, Co, Fe, Cu); S and S-peptide; PKA peptide and PKA; polyArg (6-10 Arg) and polyGlutamic acid (10-15 amino acids); GBD and galactose; streptavidin and biotin; thioredoxin and polyglutamic acid (10-15 amino acids); polyAsp and polyarginine (10-15 amino acids); and KSI and polyphenylalanine or polyleucine (10-30 amino acids).

Methods of constructing and expressing genes that encode fusion proteins are well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual*(2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (2000 Supplement) (Ausubel); Cashion et al., U.S. Pat. No. 5,017,478; and Carr, European Patent No. 0,246,864.

The mobile detectable analyte binding reagent may be, or form a portion of, an antibody or antibody fragment that binds specifically to the analyte. Antibodies useful with the present invention include, for example, intact antibodies, Fab, F(ab')$_2$, Fv, Fd, Fd' and scFv structures. In an exemplary embodiment, the antibodies are, or are derived from, IgG antibodies, IgM antibodies, or mixtures thereof. The antibodies are typically essentially free of association with antibodies capable of binding with non-analyte molecules. The antibodies may be polyclonal or monoclonal. Antibodies may be commercially available or may be obtained by mouse ascites, tissue culture or other techniques known to the art. A typical description of hybridoma procedure for the production of monoclonal antibodies may be found in Wands, J. R., and V. R. Zurawski, *Gastroenterology* 80:225 (1981); Marshak-Rothstein, A., et al.; *J. Immunol.* 122:2491 (1979); Oi, V. Y. and L. A. Herzenberg, "Immunoglobulin Producing Hybrid", Mishell, B. B. and S. M. Shiigi (eds.) Selected Methods in Cellular Immunology, San Francisco: W. H. Freeman Publishing, 1979; and U.S. Pat. No. 4,515,893 issued to Kung, et al. The use of mixtures of monoclonal antibodies of differing antigenic specificities or of monoclonal antibodies and polyclonal antibodies may be employed. Regardless of the particular source or type of antibodies, however, it is preferred that they be generally free of impurities. The antibodies may be purified by column chromatographic or other conventional means but are preferably purified according to known affinity purification techniques.

Useful antigens and haptens include those materials, whether natural or synthesized, which present antigenic determinants for which the analyte antibodies are specifically reactive when presented on the chromatographic strip materials of the invention. Synthesized antigens include those which are constructed according to conventional chemical syntheses as well as those constructed according to recombinant DNA techniques. Antigen materials may also be labeled with enzymes and colloidal particles according to the invention and used in sandwich type assays for the detection of antibody analytes or in competition assays for the detection of antigen analytes.

In some embodiments, the mobile detectable analyte binding reagent includes a nucleic acid. Thus, the devices of the present invention are useful in the practice of a wide range of nucleic acid hybridization assays. DNA and RNA hybridization materials useful in practicing the present invention include DNA and RNA polynucleotide probes having base sequences generally complementary to those of analyte gene materials. The probes of the invention will generally have between about 17 and about 10,000 bases and preferably between about 20 and about 5,000 bases. The probes need not be perfectly complementary to the base sequences of analyte gene materials and will generally hybridize provided about 70% or greater homology exists between the base sequences. Conditions relating to DNA and RNA hybridization are disclosed generally in Crosa, et al., *J. Bact.* 115(3), 904-911 (1973). Polynucleotide probe materials may be obtained according to techniques well known in the art. See, e.g., Kornberg, *DNA Replication*, W. H. Freeman and Co., San Francisco, 670-679 (1978); Dallas, et al., *J. Bacteriol.* 139, 850-858 (1979) and So, et al., Nature, 277, 453-456 (1979).

Detectable Labels

The mobile detectable analyte binding reagents of the present invention optionally include a detectable label. Any appropriate label is useful in the current invention, including, for example, luminescent labels, radioactive isotopic labels, enzymatic labels, and other labels well known in the art. Useful labels may be detectable by spectroscopic, photochemical, biochemical, immunochemical, electrical, magnetic, electromagnetic, optical or chemical means. Exemplary labels include magnetic bead labels (e.g., Dynabeads™); fluorescent dye labels (e.g., fluorescein isothiocyanate, texas red, rhodamine, green fluorescent protein, and the like); radiolabels (e.g., $H^3$, $I^{125}$, $S^{35}$, $C^{14}$, or $P^{32}$); enzyme labels (e.g., horse radish peroxidase, alkaline phosphatase and others commonly used in an ELISA); colorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; up-converting reporter labels; carbon black labels; and semi-conducting particle labels (e.g. quantum dot conjugates made from nanometer-scale crystal of semiconductor material (CdSe) coated with an additional semiconductor shell (ZnS)). Patents teaching the use of such labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

A variety of fluorescent labels can be incorporated into the compositions of the invention. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

Means of detecting such labels are well known to those of skill in the art. Thus, for example, radiolabels may be detected using photographic film or scintillation counters, and fluorescent markers may be detected using a photodetector to detect emitted illumination. Enzymatic labels are typically detected by providing the enzyme with a substrate and detecting the reaction product produced by the action of the enzyme on the substrate, and calorimetric labels are detected by simply visualizing the colored label.

Detectable labels may be associated with the mobile detectable analyte binding reagents by any appropriate means, including, for example, covalent bonding, hydrogen bonding, van der Waal forces, π bond stacking, hydrophobic interactions, and ionic bonding.

The detectable labels may be covalently attached to the mobile detectable analyte binding reagents of the present invention using a reactive functional group, which can be located at any appropriate position. When the reactive group is attached to an alkyl, or substituted alkyl chain tethered to an aryl nucleus, the reactive group may be located at a terminal position of an alkyl chain. Reactive groups and classes of reactions useful in practicing the present invention are generally those that are well known in the art of bioconjugate chemistry. Currently favored classes of reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the labeled mobile detectable analyte binding reagents. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Linkers may also be employed to attach the detectable labels to the mobile detectable analyte binding reagents. Linkers may include reactive groups at the point of attachment to the detectable label and/or the mobile detectable analyte binding reagents. Any appropriate linker may be used in the present invention, including substituted or unsubstituted alkylene, substituted or unsubstituted heteroalkylene, substituted or unsubstituted cycoalkylene, substituted or unsubstituted heterocycloalkylene, substituted or unsubstituted arylene, and substituted or unsubstituted heteroarylene. Other useful linkers include those having a polyester backbone (e.g. polyethylene glycol), nucleic acid backbones, amino acid backbones, and derivatives thereof. A wide variety of useful linkers are commercially available (e.g. polyethylene glycol based linkers such as those available from Nektar, Inc. of Huntsville, Ala.).

The detectable label may also be non-covalently attached to the mobile detectable analyte binding reagents using any appropriate binding pair. Binding pairs are discussed above in the context of analyte-mobile detectable analyte binding reagent interactions and are equally applicable to attaching a detectable label to a mobile detectable analyte binding reagent.

Assay Zone

The assay zone includes an immobilized assay reagent capable of immobilizing the mobile detectable analyte binding reagent. Typically, the immobilized assay reagent specifically binds to the mobile detectable analyte binding reagent, analyte, or mobile reagent-analyte complex.

A wide variety of immobilized assay reagents may be used to implement an array of lateral flow device formats. For example, the immobilized assay reagent may form half of a binding pair. Binding pairs are discussed above in the context of mobile reagent-analyte complexes and are equally applicable to the binding of immobilized assay reagents to the mobile detectable analyte binding reagent, analyte, or mobile reagent-analyte complex. Exemplary binding pairs include any known specific ligand and receptor pair found in nature or constructed using recombinant techniques (e.g. fusion proteins) or immunonological methods. Therefore, immobilized assay reagents include any appropriate biomolecule, such as peptides, proteins, carbohydrates, steroids, nucleic acids, sugars (including simple and complex sugars), and natural or unnatural derivatives thereof.

In an exemplary embodiment, the lateral flow chromatographic device provides a format conducive to a sandwich-type assay. In this embodiment, the immobilized assay reagent is specifically reactive with the analyte and not specifically reactive with the mobile detectable analyte binding reagent. Thus, the immobilized assay reagent is capable of binding the analyte. Typically, the mobile detectable analyte binding reagent includes a detectable label. Therefore, where the mobile detectable analyte binding reagent binds to the analyte to form a mobile reagent-analyte complex, the immobilized assay reagent will bind to the analyte portion of the mobile reagent-analyte complex to form an immobilized mobile reagent-analyte complex. Detection of the detectable label within the assay zone indicates the presence of the analyte in the sample.

In another exemplary embodiment, the lateral flow chromatographic device provides a format conducive to a competition-type assay. In this embodiment, the immobilized assay reagent is specifically reactive with the mobile detectable analyte binding reagent and not specifically reactive with the analyte. For example, the immobilized assay reagent may bind to substantially the same site on or within the mobile detectable analyte binding reagent as the analyte. Thus, when the analyte is bound to the mobile detectable analyte binding reagent, binding of the immobilized assay reagent the mobile detectable analyte binding reagent is substantially reduced. Typically, the mobile detectable analyte binding reagent includes a detectable label. Detection of the detectable label within the assay zone indicates the absence or low concentration of analyte in the sample. In a related embodiment, the immobilized assay reagent is an immobilized analyte or derivative thereof. In another related embodiment, the lateral flow chromatographic device further comprises a control zone, which is discussed below.

A variety of methods may be employed to immobilize the assay reagents of the present invention to the chromatographic medium. Useful techniques include covalent and non-covalent binding, including the use of binding pairs and reactive functional groups discussed above in the context of attaching detectable labels to mobile detectable analyte binding reagents.

Control Zone

The lateral flow chromatographic devices of the present invention may optionally include a control zone. The control zone includes an immobilized capture reagent that immobilizes a reagent having a detectable label, such as the mobile detectable analyte binding reagent. The control zone is downstream of the assay zone and in fluid communication with the assay zone upon wetting of the chromatographic medium.

The mobile detectable analyte binding reagent may be immobilized by any appropriate means, including covalent and non-covalent binding (e.g. covalent bonding, hydrogen bonding, van der Waal forces, $\pi$ bond stacking, hydrophobic interactions, and ionic bonding). Thus, binding pairs and reactive functional groups discussed above are equally applicable to the immobilized capture reagents.

In some embodiments, the immobilized capture reagent binds directly to the mobile detectable analyte binding reagent. In other embodiments, the immobilized capture reagent immobilizes the mobile detectable analyte binding reagent by binding to a reagent that is bound to the mobile detectable analyte binding reagent. The reagent that is bound to the mobile detectable analyte binding reagent is also referred to herein as an immobilization tag.

A wide variety of immobilized capture reagents are useful in binding to the immobilized capture reagent or the immobilization tag, including those reagents making up one half of a binding pair, as discussed above, as well as non-specific binders, such as protein A, protein G, and poly-L-lysine. For example, where the mobile detectable analyte binding reagent or immobilization tag includes an antibody or antibody fragment having an Fc region, then the immobilized capture reagent may be an Fc binder such as protein G, protein A, or recombinant protein A/G (a gene fusion product secreted from a non-pathogenic form of Bacillus which contains four Fc binding domains from protein A and two from protein G). Where the mobile detectable analyte binding reagent or immobilization tag is a nucleic acid, the immobilized capture reagent may include a nucleic acid that is capable of hybridizing to the mobile detectable analyte nucleic acid or immobilization tag nucleic acid. The immobilized capture reagent may also include a general binding agent, such as poly-L-lysine, that binds to the immobilization tag or the mobile detectable analyte.

In some embodiments, the immobilization reagent is a blocking reagent or a biomolecule, that is bound to some portion of the mobile detectable analyte binding reagent (e.g. the colloidal gold label). In related embodiments, the immobilized capture agent is an anti-BSA antibody, an anti-biomolecule antibody, or a general binder, such as poly-L-lysine.

As described above, the immobilized capture reagent may immobilize the mobile detectable analyte binding reagent, either alone or in combination with other reagents attached thereto (such as an analyte or immobilization tag). Thus, the immobilized capture reagent may bind to the immobilization reagent, and/or the mobile detectable analyte binding reagent portion of the mobile reagent-analyte complex. Thus, the immobilized capture reagent may immobilize the mobile detectable analyte binding reagent in the presence, and/or in the absence, of the analyte. Typically, the mobile detectable analyte binding reagent includes a detectable label. Therefore, the detection of the detectable label confirms the presence of the mobile detectable analyte thereby indicating that the lateral flow chromatographic device is functioning properly.

In some embodiments, the reagent having a detectable label is not the mobile detectable analyte binding reagent. Rather the reagent is simply a mobile control reagent having a detectable label. The mobile control reagent may be, or include, an immobilization tag as described above. Immobilization and subsequent detection of the mobile control reagent indicates that the lateral flow chromatographic device is functioning properly.

Labeling Zone

The lateral flow chromatographic device optionally includes a labeling zone. The labeling zone contains a detectable labeling reagent capable of binding to the mobile detectable binding reagent. The labeling zone is downstream of the analyte binding zone and upstream of the assay zone. The labeling zone is in fluid communication with the sample release zone and the assay zone upon wetting of the chromatographic medium. Therefore, as the mobile detectable binding reagent passes through the labeling zone, the detectable labeling reagent attaches to form a labeled mobile detectable binding reagent.

Useful detectable labels and methods for their attachment to the mobile detectable binding reagent are discussed above and are equally applicable to the detectable labeling reagents.

Sink Zone

The lateral flow chromatographic device optionally includes a sink zone downstream of, and in fluid communication with the assay zone upon wetting of the chromatographic medium. The sink zone includes a sorbent material. The function of the sink zone is to aid in the capillary movement of a sample through the lateral flow chromatographic device. Therefore, any appropriate sorbent material (i.e. adsorbent and/or absorbent) is useful as a component of the sink zone. Adsorbent materials are insoluble materials that coat liquid on the material surface, including pores and capillaries, without substantial swelling (e.g., less than about 50%). Absorbent materials are insoluble materials that draw in and retain liquid causing substantial swelling (e.g. more than about 50%).

A wide variety of sorbent materials are known in the art and are applicable to the current invention, including, for example, inorganic microporous sorbent materials (e.g., zeolites, clays, silica gels, activated alumina, and the like), polyesters, coated plastics, coated rubbers, sponges (both natural and synthetic), and paper products (e.g. cellulose and nitrocellulose based materials).

Chromatographic Media

Chromatographic media useful with the present invention include those chromatographic substrate materials having capillarity and the capacity for chromatographic solvent transport of non-immobilized reagents and reactive sample components by means of a selected chromatographic solvent. The chromatographic substrate materials used with the invention may be in the form of strips or other forms including, but not limited to, particles or gel materials in a chromatographic column. While a wide variety of chromatographic strip materials such as woven and non-woven fibrous materials used for paper chromatography are suitable for use with the invention, microporous or microgranular thin layer chromatography substrates are also useful and may improve the speed and resolution of the assays. When used in the final test format, the materials should preferably be inert and generally not reactive physically or chemically with any of the sample components, reagents, colloidal particle labels, buffers or reaction products. The addition of materials, such as polyvinyl alcohol or any suitable blocking agent can be used to block a reactive material while the test runs or prior to running the test.

Thin layer chromatographic substrate materials particularly suitable for use with the present invention include granular thin layer chromatographic materials such as silica or microgranular cellulose. Useful non-granular microporous materials include microporous cellulose esters, for example, esters of cellulose with an aliphatic carboxylic acid, such as an alkane carboxylic acid, having from 1 to 7 carbon atoms, e.g., acetic acid, propionic acid, or any of the butyric acids or valeric acids. Also useful are microporous materials made from nitrocellulose, by which term any nitric acid ester of cellulose is intended. Suitable materials include nitrocellulose in combination with any of the carboxylic acid cellulose esters. Thus, pure nitrocellulose esters can be used as consisting of an ester of cellulose having approximately 3 nitric groups per 6 carbon atoms (e.g. a Type SMWP material (Millipore Corp., Bedford, Mass.)).

The various chromatographic substrate materials may be used as such in suitable shapes such as films, strips or sheets. They may also be coated onto or bonded or laminated to appropriate inert support materials such as paper, glass, plastic, metal or fabrics (e.g. Mylar). The support material may provide structural support to the chromatographic substrate material as well as prevent evaporation of reagent and solvent materials during the assay procedure. Cover plates may also be fashioned of such inert materials. Cover plates, although not required for practice of the invention, lend additional structural support and further prevent evaporation of reagent and solvent materials during the assay procedure. Such cover plates may be transparent for viewing the progression of the assay and may comprise ports for addition of sample materials, chromatographic solvent or reagents.

The chromatographic medium upon which the assays are conducted may be any shape or size. In an exemplary embodiment, the medium is a strip of thickness in the range of from about 0.01 mm to about 0.5 mm. In a related embodiment, the thickness is about 0.1 mm. The strips may vary widely in their other dimensions and may be kept fairly small in order to shorten the assay development time and minimize material usage. When the strips are extremely small in size they may be attached to a suitable handle or holder in order to aid in handling and observation of results. Strips approximately 2-10 mm wide and up to 100 mm long have been found to be particularly suitable in the fabrication of single pathway devices.

The pore size may vary within wide limits. The pore size is between about 0.05 $\mu$m and 20 $\mu$m. In a related embodiment, the pore size is about 5 $\mu$m. Pore size is limited on the lower end by the size of the transported analytes, reagents and colloidal particle labels. If the pore size is too small, assay materials will be transported slowly or not at all. On the higher end, pore size is limited by binding capacity.

The chromatographic transport may be rapid with the transport and assay being completed within less than five minutes, and possible less than or about two minutes. Chromatographic transport should not be so rapid that specific binding capacity is lost as reagents do not have time to specifically bind. The combination of pore size and substrate thickness may thus be varied according to the characteristics of the chromatographic solvents, specific reagents, sample materials and detectable labels used in order to obtain the desired speed and resolution.

In forming the strip materials of the present invention, it may be desirable to minimize irregularities in the materials or in the edges of the materials which might cause uneven flow through the material. Means of fashioning the strip materials include the use of a paper cutter with a tungsten carbide rotary blade. Alternatively, a laser cutting device may be used that is suitable for use in mass production techniques.

As discussed above, various reagents may be immobilized (e.g. immobilized capture reagent and immobilized and immobilized assay reagent). Where the media is nitrocellulose or a mixed nitrocellulose ester, immobilization of reagents may not require any specific linkage. As discussed above, various reactive groups may be used for other materials and reagents, including functionalization with materials such as carbonyldiimidazole, glutaraldehyde or succinic acid, or treatment with materials such as cyanogen bromide. Other suitable reactions include treatment with Schiff bases and borohydride for reduction of aldehydic, carbonyl and amino groups. DNA, RNA and certain antigens may be immobilized against solvent transport by baking onto the chromatographic material. For nucleic acids, baking may be carried out at temperatures ranging from about 60° C. to about 120° C. for times varying from about five minutes to about 12 hours, but preferably at about 80° C. for about two hours.

In some embodiments, components of the present invention (e.g. binding reagents, bulking material, assay reagents, labeling reagents, and/or capture reagents) are impregnated and dried onto the chromatographic media of the devices. The components may be resolubilized upon wetting and subsequently transported by means of conventional chromatographic solvent systems. The ability to impregnate chromatographic media with the device components, which may then be resolubilized, makes possible the practice of a variety of assay procedures.

Release Zone

As discussed above, the purpose of the sample release zone of the present invention is to provide reagent stability and/or controlled release of the reagents. Controlled release of the reagents may provide additional time for the components (e.g. the analyte and the mobile detectable analyte binding reagent) of the test device to interact when wetted, thereby providing improved detectability.

The release zone is upstream of the assay zone and in fluid communication with the assay zone upon wetting of the chromatographic medium. The release zone may completely or partially overlap with the analyte binding zone. Thus, the release zone may be combined with the analyte binding zone to form a single zone, also referred to herein as a release-binding zone. The release zone may also partially or completely overlap with the labeling zone. In an exemplary embodiment, a single zone is formed by combining the release zone and the labeling zone, also referred to herein as a labeling release zone.

The sample release zone includes a bulking material. The bulking material includes a starch reagent (as described below) and optionally additional reagents, such as salts, buffers, surfactants, blocking agents and biomolecules (such as starch, nucleic acid, protein, and amino acids). Desirable bulking materials provide stability and flow release of the reagents of the present invention.

Surfactants are useful as additional reagents in the bulking material. Exemplary surfactants include, for example, non-ionic surfactants and ionic surfactants. Non-ionic surfactants do not ionize in aqueous solutions. Exemplary non-ionic surfactants include sodium deoxycholate, octylglucoside, digitonin, octaethyleneglycol mono n-dodecyl ether (C12E8), lubrol, polyoxyethylated octyl phenol (Triton X-100), ethylphenolpoly-(ethyleneglycolether) (Nonidet P-40), [Octylphenoxy]polyethoxyethanol (Nonidet P-40 substitute), Polyoxyethylene Sorbitan Monooleate (polyoxyethylenesorbitanmonooleat) (Tween 80), polyoxyethylene sorbitan monolaureate (Tween-20), BRIG 35, dodecyl maltopyranoside, heptyl thioglucopyranoside, ethylenoxide and propylenoxide block-copolymer surfactants such as Pluronic and Tetronic surfactants available from BASF (e.g. Pluronic F-127 and Tetronic T1307), Isotridecyl(PEG-ether)$_8$ (also referred to as Genapol X-080), N-alkanoyl-N-methylglucamide surfactants (e.g. the MEGA series surfactant including MEGA 9 AND MEGA 10), and the like. Ionic surfactants include anionic surfactants, cationic surfactants, and amphoteric surfactants. Useful anionic surfactants include, for example, sodium dodecyl sulfate, cholate and deoxycholate, and the like. Exemplary cation surfactants include cetyltrimethyl-ammonium bromide (CTAB) and the like. Amphoteric surfactants useful in the present invention include, for example, LysoPC, CHAPS, Zwittergent 3-14, and the like.

In an exemplary embodiment, the surfactant is selected from octylglucoside, digitonin, C12E8, lubrol, Triton X-100, Nonidet P-40, Tween 80, Tween-20, BRIG 35, dodecyl maltopyranoside, heptyl thioglucopyranoside, Pluronic F-127, Genapol X-080, Tetronic T1307, and MEGA 10. In another exemplary embodiment, the surfactant is Tetronic T1307. The concentration of surfactant in the bulking material may be from about 0.01% to about 10%. In an exemplary embodiment, the concentration of the surfactant is between 1% and 5%. In another exemplary embodiment, the concentration is about 1.5%.

Buffers are also useful as additional reagents in the bulking material. One skilled in the art will recognize that the choice of buffer will depend upon the solvent used in the assay and the desired pH. For biological samples, the desired pH is typically between 5.0 and 9.0. In an exemplary embodiment, the desired pH is between 6.0 and 8.0. In another exemplary embodiment, the desired pH is between 7.0 and 8.0. In yet another exemplary embodiment, the desired pH is about 8.0. Exemplary buffers include N-[2-hydroxy-1,1-bis(hydroxymethyl)ethyl]glycine, and tris(hydroxymethyl)aminomethane (Tricine), acetate, borate, citrate, HEPES (N-2-hydroxyethylpiperazine-N'-2-ethanesulfonic acid), BES (N,N-bis[2-hydroxyethyl]-2-amino-ethanesulfonic acid), TES (N-tris[Hydroxymethyl] methyl-2-aminoethanesulfonic acid), MOPS (morpholine propanesulphonic acid), PIPES (piperazine-N,N'-bis[2-ethane-sulfonic acid]), and MES (2-morpholino ethanesulphonic acid). In an exemplary embodiment, the buffer is Tricine.

The bulking material may also include a blocking reagent to prevent binding of the assay components to the chromatographic media. The choice of blocking reagent will depend on the solvent used in the assay, the analyte to be detected, the pH of the solution, and the reactivity of the blocking agents. Useful blocking agents include meta-soluble proteins (e.g., casein, zein as disclosed in U.S. Pat. No. 6,534,320), alcohol blocking reagents (e.g. polyvinyl alcohol (PVA)), and soluble protein blocking agents. Soluble protein blocking agents include, for example, serum albumin (including bovine, horse, sheep, and goat); hydrolyzed proteins (including hydrolyzed casein); and commercially available polypeptides, proteolytic digest, and synthetic peptide (e.g. those commercially available, for example, from Sigma Chemicals or Bachem Inc.). In an exemplary embodiment, the blocking agent is polyvinyl alcohol. The concentration of the blocking reagent may range from about 0.01% to about 20%. In an exemplary embodiment, the concentration is between about 0.05% to about 5%. In another exemplary embodiment, the concentration is about 0.1%.

Flow aregents may also be included in the bulking material to adjust the smooth and even release of the assay reagents. Useful flow agents include polymers and polymeric particles such as polyvinylpyrrolidone (e.g. PVP-10). In an exemplary embodiment, the concentration of the flow agent is between about 0.01% to about 0.1%. In another exemplary embodiment, the concentration of the flow reagent is about 0.05%.

A wide variety of salts are useful as additional reagents in the bulking material of the present invention, including, for example, potassium gluconate, potassium benzoate, sodium benzoate, potassium tartrate, sodium tartrate, potassium sodium tartrate, sodium borate, potassium borate, potassium sulfate, sodium acetate, potassium acetate, ammonium acetate, potassium oxalate, sodium oxalate, sodium citrate, sodium ascorbate, sodium sorbate, potassium sorbate, potassium sorbitol, sodium sorbitol, potassium glutamate, sodium glutamate, ammonium glutamate, ammonium citrate lactic acid, succinic acid, sodium propionate, potassium propionate, and malonic acid.

Nucleic acids useful as additional reagents in the bulking material include DNA, RNA, and derivatives thereof.

In an exemplary embodiment, the bulking material does not contain a sugar. In another exemplary embodiment, the bulking material does not include a non-sugar sweetener, such as those disclosed in co-pending U.S. patent application Ser. No. 10/946,963 (e.g. artificial sweeteners such as aspartame, saccharin, acelsulfame, sucralose, and the like).

In another exemplary embodiment, the bulking material does not include a sugar or a non-sugar sweetener.

Starch Reagents

A variety of starch reagents are useful in the present invention, including starches found in nature (such as glycogen, amylose, amylopectin, and cellulose) as well as their hydrolyzed equivalents, also referred to herein as "hydrolyzed starch reagents." One of skill in the art will recognize that starch reagents may be hydrolyzed to varying degrees. Therefore, hydrolyzed starch reagents of the present invention include partially hydrolyzed starches.

The glucose monomers in starch reagents are covalently bonded together through glycosyl linkage groups. The glycosyl linkages may be alpha linkages or beta linkages. In an exemplary embodiment, the glycosyl linkages are alpha linkages. In another exemplary embodiment, glucose units are D-glucose units.

Hydrolyzed starches are typically produced through controlled decomposition of suspensions of starch in an acid medium. Starch hydrolysis products are commonly characterized by their degree of hydrolysis, expressed as dextrose equivalent (DE), which is the percentage of reducing sugar calculated as dextrose on dry-weight basis.

In an exemplary embodiment, the starch reagent is a dextrose reagent, such as a maltodextrin reagent. Maltodextrin is a partially hydrolyzed starch product. The United States Food and Drug Administration defines maltodextrin as (21 CFR paragraph 184.1444): a non-sweet, nutritive saccharide polymer that consists of D-glucose units linked primarily by alpha-1,4 bonds and that has a DE (dextrose equivalent) of less than 20. In the 40 years since the first introduction, a range of commercial maltodextrins has become available and is used in a wide range of applications. The dextrose equivalent of a maltodextrin has been shown to be inadequate to predict the product performance in various applications (see Chronakis, *Critical Reviews in Food Science* 38: 599-637 (1988); Chronakis, *Lebensmittel Wissenschaft und Technologie* 30: 36-44 (1997)). Industrially produced maltodextrins (with a certain average degree of polymerization) normally consist of a broad distribution of both linear and branched (e.g. alpha(1-6) linkages) saccharides.

The properties of maltodextrin differ drastically from simple sugars. For example, maltodextrin has a higher viscosity, a lower hygroscopicity, a higher wet binding, a lower dry binding, a higher crystal growth inhibition, lower solubility, and higher osmolality than simple sugars. In addition, maltodextrin is non-sweet. Therefore, one skilled in the art would not expect maltodextrin to have similar releasing and stability properties as simple sugars.

Useful hydrolyzed starch reagents include maltodextrin reagents of various lengths. In an exemplary embodiment, the maltodextrin reagent is maltodextrin having a dextrin equivalence (DE) of less than or equal to 20. In a related embodiment, maltodextrin has a dextrose equivalence from 5 to 20. In another related embodiment, the maltodextrin has a DE from 11 to 18. In another related embodiment, the maltodextrin has a DE of 11 or 18. Typically, the concentration of starch reagent in the bulking material rangers from 0.01% to 60% (w/v). In an exemplary embodiment, the concentration ranges from 1% to 20%. In another exemplary embodiment, the concentration is at least 2.5%. In a related embodiment, the concentration ranges from 2.5% to 20%. In a further related embodiment, the concentration ranges from 2.5% to 15%. In another exemplary embodiment, the concentration is about 15%.

Methods

In another aspect, the present invention provides a method of stabilizing a protein (e.g. an antibody) in a dry state. The method includes contacting the antibody with a bulking material. Bulking materials are described above and are equally applicable to the present methods. The bulking material includes a starch reagent. In an exemplary embodiment, the starch reagent is a maltodextrin reagent.

In another aspect, the present invention provides methods of determining the presence of an analyte in a sample using the test device described above. The method includes contacting the analyte binding zone of the test device of the present invention with a sample and allowing the sample to flow from the sample release zone to the assay zone. The presence of the analyte is determined by detecting the presence or absence of the detectable label associated with the mobile detectable analyte binding reagent as described above.

Kits

The present invention further includes kits for use in detecting the presence of an analyte in a sample. The kit includes a test device of the present invention. Test devices are discussed in detail above and are equally applicable to the kits of the present invention.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of test devices of the present invention are equally applicable to the kits and methods of the present invention described herein. All publications, patents, and patent applications cited herein are hereby incorporated by reference in their entirety for all purposes.

EXAMPLES

Example 1

The purpose of this experiment was to examine concentrations of maltodextrin for use in the bulking reagents of the present invention.

A stock solution of THC gold was made by coating gold colloid at 0.8 μgm/OD/mL with monoclonal anti-THC (MedTox clone) for 5 minutes at room temperature (RT) followed by blocking for NSB with 30 μgm/OD of BSA (Sigma Chemical) for 10 minutes at room temperature. The THC gold was diluted in varying concentrations of maltodextrin (Carbo Gain from Now Sports), 1% Tetronic T1307 (BASF), 100 mM Tricine (Sigma Chemical), 0.1% polyvinyl alcohol (10 kd, Sigma Chemical), 0.05% PVA-10 (10 kd, Sigma Chemical) to 3 OD/mL and 15 microliters of this mixture spotted onto 5 mm wide by 22 mm long glass fiber membranes (Millipore GF), dried at 1 hour at 57° C., tested using a THC negative urine, then subjected to overnight baking at 57° C. and retested using a negative urine sample. Readings were by visual examination at 7 minutes.

TABLE 1

| Reagent | THC(−) 1 hr 57° C. | THC(−) 3-5 day@57° C. |
|---|---|---|
| None | ++ to +++ | + − |
| 1.25% Maltodextrin | ++ | + − |
| 2.5%" | ++ | + − to + |
| 5%" | ++ | + |
| 10%" | ++ | + |
| 15%" | ++ | ++ |

Notes:
A − + signal indicates the line is barely visible, a + − indicates a light line, a + signal is a line that is easily seen. These are graded up to a ++++ line, which is as dark as a control line (nearly black).

As shown in Table 2, maltodextrin from a commercial source aids in reagent stability at concentrations at or above 2.5%.

Example 2

The purpose of this experiment was to test size ranges of maltodextrin for use in a bulking material of the present invention.

Prepared PCP colloidal gold using a MedTox monoclonal anti-PCP antibody conjugated to colloidal gold at 4 μgm/OD/mL (pH 8) and THC colloidal gold using a MedTox monoclonal anti-THC antibody at 0.8 μm/OD/mL (pH 8) as previously described. Tested colloidal golds at 3 OD/mL using maltodextrin (Cargill) as a starch reagent agent for its ability to stabilize these labile monoclonals with a dextrose equivalence rating of 11 and 18 in a solution of 1.5% Tetronic T1307, 0.1% PVA-10, 0.05% PVP-10, and 100 mM Tricine pH 8.0. Tested 15 microliters spotted onto 5 mm by 22 mm Millipore GF membrane baked at 1 hr vs ON at 57° C.

TABLE 2

| Reagent | PCP-4 | THC.8 | Comments |
|---|---|---|---|
| Baked 1 hour at 57° C. (initial look) | | | |
| 15% DE11 | ND | ++ | Slow gold release |
| 15% DE18 | ND | ++ | Slow gold release |
| Baked 2 days at 57° C. | | | |
| 15% DE11 | ND | + to ++ | |
| 15% DE18 | ND | ++ | |

ND = not done

As shown in Table 4, DE11 and DE18 provided stabilization.

What is claimed is:

1. A test device for detecting the presence of an analyte in a sample, said device comprising a chromatographic medium comprising:
   (a) an analyte binding zone comprising a mobile detectable analyte binding reagent capable of binding to said analyte;
   (b) an assay zone comprising an immobilized assay reagent capable of immobilizing said mobile detectable analyte binding reagent, wherein said assay zone is in fluid communication with said analyte binding zone upon wetting said chromatographic medium; and
   (c) a sample release zone comprising a bulking material wherein said bulking material comprises a starch reagent, wherein said sample release zone is upstream of said assay zone and in fluid communication with said assay zone upon wetting said chromatographic medium.

2. The device of claim 1, wherein said immobilized assay reagent is capable of binding to said analyte.

3. The device of claim 1, wherein said immobilized assay reagent is capable of binding to said mobile detectable analyte binding reagent, wherein the binding of said mobile detectable analyte binding reagent to said immobilized assay reagent is reduced when said analyte is bound to said mobile detectable analyte binding reagent.

4. The device of claim 1, further comprising, downstream of, and in fluid communication with said assay zone, a control zone comprising an immobilized capture reagent that immobilizes said mobile detectable analyte binding reagent in the presence, and in the absence, of said analyte.

5. The device of claim 1, further comprising, downstream of, and in fluid communication with said assay zone, a control zone comprising an immobilized capture reagent that immobilizes a mobile control reagent, said mobile control reagent comprising a detectable label.

6. The device of claim 1, wherein said sample release zone completely or partially overlaps with said analyte binding zone.

7. The device of claim 6, further comprising, downstream of said analyte binding zone and upstream of said assay zone, a labeling zone in fluid communication with said sample release zone and said assay zone upon wetting of said medium, said labeling zone comprising a detectable labeling reagent capable of binding to said mobile detectable analyte binding reagent.

8. The device of claim 7, wherein said detectable labeling reagent comprises a detectable label selected from the group consisting of radioisotope label, luminescent label, magnetic bead label, fluorescent dye label, enzyme label, colloidal metal label, colored glass bead label, colored latex bead label, up-converting reporter label, carbon black label, and semiconducting particle label.

9. The device of claim 1, wherein said sample release zone is downstream of said analyte binding zone and is in fluid communication with said analyte binding zone upon wetting of said medium.

10. The device of claim 9, wherein said sample release zone further comprises a detectable labeling reagent capable of binding to said mobile detectable analyte binding reagent.

11. The device of claim 1, wherein said mobile detectable analyte binding reagent comprises a detectable label.

12. The device of claim 11, wherein said detectable label is selected from the group consisting of radioisotope label, luminescent label, magnetic bead label, fluorescent dye label, enzyme label, colloidal metal label, colored glass bead label, colored latex bead label, up-converting reporter label, carbon black label, and semiconducting particle label.

13. The device of claim 1, further comprising a sink zone downstream of, and in fluid communication with said assay zone upon wetting of said medium, wherein said sink zone comprises a sorbent material.

14. The device of claim 1, wherein said starch reagent is a maltodextrin reagent.

15. The device of claim 1, wherein said starch reagent is a hydrolyzed starch reagent.

16. The device of claim 15, wherein said hydrolyzed starch reagent is a hydrolyzed maltodextrin reagent.

17. The device of claim 1, wherein said starch reagent is a maltodextrin reagent having a dextrose equivalence less than or equal to 20.

18. The device of claim 1, wherein said starch reagent is a maltodextrin reagent having a dextrose equivalence from 5 to 20.

19. The device of claim 1, wherein said starch reagent is a maltodextrin reagent having a dextrose equivalence of 11 or 18.

20. The device of claim 1, wherein said starch reagent is a maltodextrin reagent having a dextrose equivalence of 18.

21. The device of claim 1, wherein said bulking material further comprises one or more additional reagents selected from the group consisting of an amino acids, salts, surfactants, blocking reagents, flow reagents, soluble proteins, buffers and nucleic acids.

22. The device of claim 21, wherein said salt contains one or more salt reagents selected from the group consisting of potassium gluconate, potassium benzoate, sodium benzoate, potassium tartrate, sodium tartrate, potassium sodium tartrate, sodium borate, potassium borate, potassium sulfate, sodium acetate, potassium acetate, ammonium acetate, potassium oxalate, sodium oxalate, sodium citrate, sodium ascorbate, sodium sorbate, potassium sorbate, potassium sorbitol, sodium sorbitol, potassium glutamate, sodium glutamate, ammonium glutamate, ammonium citrate lactic acid, succinic acid, sodium propionate, potassium propionate, and malonic acid.

23. The device of claim 21, wherein said surfactant is a non-ionic surfactant.

24. The device of claim 21, wherein said surfactant is a propylenoxide block-copolymer surfactant.

25. The device of claim 21, wherein said buffer is a member selected from the group consisting of sodium borate, N-[2-hydroxy-1,1-bis(hydroxymethyl)ethyl]glycine, and tris(hydroxymethyl)aminomethane.

26. The device of claim 21, wherein said soluble protein is a member selected from the group consisting of serum albumin, hydrolyzed proteins, polypeptide, proteolytic digest, and synthetic peptide.

27. The device of claim 21, wherein said nucleic acid is DNA.

28. The device of claim 21, wherein said blocking reagent is polyvinyl alcohol.

29. The device of claim 21, wherein said flow reagent is polyvinylpyrrolidone.

30. A method of stabilizing a protein in a dry state comprising contacting said protein with a bulking material comprising a starch reagent.

31. The method of claim 30, wherein said starch reagent is a maltodextrin reagent.

32. The method of claim 30, wherein said starch reagent is a hydrolyzed starch reagent.

33. The method of claim 32, wherein said hydrolyzed starch reagent is a hydrolyzed maltodextrin reagent.

34. The method of claim 30, wherein said starch reagent is a maltodextrin reagent having a dextrose equivalence less than or equal to 20.

35. The method of claim 30, wherein said starch reagent is a maltodextrin reagent having a dextrose equivalence from 5 to 20.

36. The method of claim 30, wherein said starch reagent is a maltodextrin reagent having a dextrose equivalence of 11 or 18.

37. The method of claim 30, wherein said starch reagent is a maltodextrin reagent having a dextrose equivalence of 18.

38. The method of claim 30, wherein said bulking material further comprises one or more additional reagents selected from the group consisting of an amino acids, salts, surfactants, flow reagents, blocking reagents, soluble proteins, buffers and nucleic acids.

39. The method of claim 38, wherein said salt contains one or more salt reagents selected from the group consisting of potassium gluconate, potassium benzoate, sodium benzoate, potassium tartrate, sodium tartrate, potassium sodium tartrate, sodium borate, potassium borate, potassium sulfate, sodium acetate, potassium acetate, ammonium acetate, potassium oxalate, sodium oxalate, sodium citrate, sodium ascorbate, sodium sorbate, potassium sorbate, potassium sorbitol, sodium sorbitol, potassium glutamate, sodium glutamate, ammonium glutamate, ammonium citrate lactic acid, succinic acid, sodium propionate, potassium propionate, and malonic acid.

40. The method of claim 38, wherein said surfactant is a non-ionic surfactant.

41. The method of claim 38, wherein said surfactant is a propylenoxide block-copolymer surfactant.

42. The method of claim 38, wherein said buffer is a member selected from the group consisting of sodium borate, N-[2-hydroxy-1,1-bis(hydroxymethyl)ethyl]glycine, and tris(hydroxymethyl)aminomethane.

43. The method of claim 38, wherein said soluble protein is a member selected from the group consisting of serum albumin, hydrolyzed proteins, polypeptide, proteolytic digest, and synthetic peptide.

44. The method of claim 38, wherein said nucleic acid is DNA.

45. The method of claim 38, wherein said blocking reagent is polyvinyl alcohol.

46. The method of claim 38, wherein said flow reagent is polyvinylpyrrolidone.

* * * * *